(12) United States Patent
Femopase

(10) Patent No.: US 10,687,894 B2
(45) Date of Patent: Jun. 23, 2020

(54) VAGINAL REMODELING/REJUVENATION DEVICE AND METHOD

(75) Inventor: Gabriel Femopase, Cordoba (AR)

(73) Assignee: Biolitec Unternehmensbeteiligungs II AG, Vienna (AT)

( * ) Notice: Subject to any disclaimer, the term of this patent is extended or adjusted under 35 U.S.C. 154(b) by 1541 days.

(21) Appl. No.: 13/997,554

(22) PCT Filed: Dec. 29, 2011

(86) PCT No.: PCT/US2011/067938
§ 371 (c)(1),
(2), (4) Date: Aug. 6, 2014

(87) PCT Pub. No.: WO2012/092508
PCT Pub. Date: Jul. 5, 2012

(65) Prior Publication Data
US 2014/0343540 A1    Nov. 20, 2014

Related U.S. Application Data

(60) Provisional application No. 61/481,974, filed on May 3, 2011, provisional application No. 61/428,023, filed on Dec. 29, 2010.

(51) Int. Cl.
*A61B 18/22* (2006.01)
*A61B 18/20* (2006.01)
*A61B 18/00* (2006.01)

(52) U.S. Cl.
CPC .... *A61B 18/22* (2013.01); *A61B 2018/00196* (2013.01); *A61B 2018/00559* (2013.01);
(Continued)

(58) Field of Classification Search
CPC . A61B 18/20; A61B 18/22; A61B 2018/2035; A61B 2018/2036;
(Continued)

(56) References Cited

U.S. PATENT DOCUMENTS

| 5,449,354 A | * | 9/1995 | Konwitz | A61B 18/24 |
| | | | | 606/13 |
| 5,478,339 A | * | 12/1995 | Tadir | A61N 5/062 |
| | | | | 606/15 |

(Continued)

*Primary Examiner* — Ahmed M Farah
(74) *Attorney, Agent, or Firm* — BJ Associates; Bolesh J Skutnik

(57) ABSTRACT

A device and method for treating a vagina's anatomic, functional and aesthetic conditions are disclosed. Device comprises a laser energy source which conveys laser energy through an optical fiber handpiece. A cylindrical/penis shaped device/applicator is specially designed for safe and accurate irradiation of determined parts of vaginal mucosa. Applicator has an inner hollow path through which optical fiber is inserted to irradiate interior vaginal tissue. Irradiated mucous tissue contracts, reducing vaginal radius and during penetration in sexual intercourse it embraces penis more tightly. Sensitivity is substantially improved and sexual intercourse is more pleasurable for both partners. In one embodiment, a 1470 nm diode laser source is used. In another embodiment, a vagina's outer dimensions are accurately measured and surgery is performed to achieve dimensions according to certain aesthetic and functional criteria. Minimum pain and risk of side effects are experienced with this ambulatory procedure performable in a physician's office.

13 Claims, 3 Drawing Sheets

(52) U.S. Cl.
CPC ............... *A61B 2018/00577* (2013.01); *A61B 2018/00982* (2013.01); *A61B 2018/20361* (2017.05); *A61B 2018/2272* (2013.01)

(58) Field of Classification Search
CPC .... A61B 2018/2255; A61B 2018/2272; A61B 2018/2277; A61B 2018/00184; A61B 2018/00196; A61B 2018/00315; A61B 2018/00559; A61B 2018/00577; A61B 2018/00589; A61B 2018/00601; A61B 2018/00607
USPC ......... 606/3, 13–17; 607/88, 89, 92, 93, 138
See application file for complete search history.

(56) References Cited

U.S. PATENT DOCUMENTS

| | | | | |
|---|---|---|---|---|
| 6,471,692 B1* | 10/2002 | Eckhouse | ............ | A61N 5/0601 606/14 |
| 7,749,162 B2* | 7/2010 | Balas | ............ | A61B 1/303 600/220 |
| 8,292,935 B2* | 10/2012 | Neuberger | ............ | A61N 5/0601 606/17 |
| 8,574,177 B2* | 11/2013 | Pryor | ............ | A61H 21/00 601/15 |
| 8,696,561 B2* | 4/2014 | Fenster | ............ | A61B 1/303 600/221 |
| 8,936,592 B2* | 1/2015 | Beck | ............ | A61B 18/22 606/15 |
| 2005/0197682 A1* | 9/2005 | Fox | ............ | A61N 5/0613 607/88 |
| 2008/0039906 A1* | 2/2008 | Huang | ............ | A61N 5/0603 607/88 |
| 2009/0240242 A1* | 9/2009 | Neuberger | ............ | A61B 18/24 606/7 |
| 2009/0287198 A1* | 11/2009 | Hanley | ............ | A61B 18/24 606/15 |
| 2010/0030020 A1* | 2/2010 | Sanders | ............ | A61B 1/00105 600/109 |
| 2010/0076526 A1* | 3/2010 | Krespi | ............ | A61N 5/0603 607/88 |
| 2013/0345686 A1* | 12/2013 | Brown | ............ | A61B 18/22 606/15 |
| 2016/0129278 A1* | 5/2016 | Mayer | ............ | A61N 5/0603 607/92 |
| 2018/0008837 A1* | 1/2018 | Zhang | ............ | A61N 5/0603 |

\* cited by examiner

VAGINAL REMODELING/REJUVENATION DEVICE AND METHOD

NATIONAL STAGE FILED UNDER 35 U.S.C. § 371

This is a national stage application and it claims priority to PCT application No. PCT/US11/67938 filed on Dec. 29, 2011, which claims the benefit of U.S. Provisional Application Ser. No. 61/481,974 filed on May 3, 2010, and U.S. Provisional Application Ser. No. 61/428,023 filed on Dec. 29, 2010 entitled "Portable Medical Laser System" by Gabriel Femopase, the entire contents of each of which are hereby incorporated by reference.

BACKGROUND OF THE INVENTION

Field of the Invention

The present invention relates to devices and medical treatments for medical and aesthetic conditions of female genitalia. More particularly, it relates to optical fiber and laser systems and methods used for the treatment of various medical and aesthetic conditions of female genitalia such as female sexual dysfunction (FSD).

State of the Art

Sexuality occupies an important part in the lives of adult men and women. It is an important health issue that affects the quality of life of many women and their partners across the world. Almost 50% of women report sexual problems at some point in their life. They may have difficulty or have lost their ability to achieve an orgasm. Some experience discomfort or even pain during sex. Many are unsatisfied with the external looks of their genitalia.

Aesthetically, there is a historically well known criterion for objectively assessing subjective features, such as beauty and perfection. At least since the Renaissance, many artists and architects have proportioned their works to approximate the golden ratio-especially in the form of the golden rectangle, in which the ratio of the longer side to the shorter is the golden ratio-believing this proportion to be aesthetically pleasing. In the human anatomy, characteristics such as harmony, proportion and symmetry have been considered with these criteria since Leonardo Da Vinci. Leonardo da Vinci's illustrations of polyhedral in De Divina Proportione (On the Divine Proportion) and his views that some bodily proportions exhibit the golden ratio, have led some scholars to speculate that he incorporated the golden ratio in his paintings. However, there are no known works which have applied such criteria or any other criteria to the human external sex organs.

Thus, a method is needed which adopts objective criteria to perform treatments focused on beautifying female genitalia.

Vaginal relaxation is a condition in which the vaginal muscles become relaxed, loosing tone, strength, control and support. The internal and external vaginal diameters can greatly increase. Thus, the vagina cannot sexually function as under normal conditions. Sexual response, defined as a set of psychological, neurophysiological, vascular and hormonal changes that take place when engaging in sexual acts, diminishes due to a reduction of sexual feelings and pleasure. Additionally, other physiological problems commonly arise, such as vaginal prolapse and consequently urinary incontinence.

Approaches to correct this are aimed at tightening the vagina's inner tissue and reducing its diameter. Some are related to delivery of liquids into the body and which solidify inside the body to yield a solid or gel to enhance the tension in vaginal tissues and pelvic floor. For instance, US Patent Application 2005/0187429 by Poppas et al presents a tissue reinforcement therapy to make the vaginal vault smaller and possibly increase and/or restore sexual gratification. Therapy involves augmenting the distal third of the vagina, the orgasmic platform, the external vaginal opening and the perineal area with an injectable, in situ polymerizing, liquid. One aspect of the invention involves a surgical adhesive used as a tissue filling or augmentation medium to decrease the internal diameter of the vagina. The surgical adhesive cures in place in the body to form an elastic, malleable solid capable of displacing tissue and thereby increasing the tone of the vagina. In U.S. Pat. No. 6,165,108 the use of a dumbbell-shaped device for exercising the musculature of the vagina is proposed. U.S. Pat. No. 6,469,016 describes the use of prostaglandins and related chemicals to temporarily affect local lubricity and also affect local muscle tone. All of these approaches have proven ineffective and there is no long-lasting effect of the therapy. US Patent Application Publication 2004/0059190 by Matlock discloses a method of colpoplasty directed to augmentation of the Grafenberg Spot area. One preferred embodiment of temporary colpoplasty uses injectable collagen obtained from a tissue bank. One embodiment of a permanent colpoplasty uses implantable grade Expanded Polytetrafluoroethylene (ePTFE). This approach does not address the problem of an augmented diameter of vagina and therefore condition persists.

Thus, a treatment is needed to effectively address vaginal relaxation and the negative consequences regarding a woman's sexual response.

Several surgical treatments are offered to women by different aesthetic medical centers, such as labiaplasty, vaginoplasty, perineoplasty, and clitoral hood reduction. Labiaplasty involves the removal of a portion of the hypertrophied labia minora and the occasionally enlarged and redundant labia majora. Clitoral hood reduction involves a size reduction of redundant or hypertrophic clitoral hood folds for cosmetic reasons or less frequently, for separation of a phimotic hood to provide more exposure of the clitoral glands to provide improved sensation. Perineoplasty is the surgical reconstruction of the vulvar vestibule, vaginal introitus, and distal vagina, whereby scarred and redundant tissue is excised, the opening attenuated, and the superficial transverse perineal and levator musculature reapproximated in the midline to elevate the perineum and pelvic floor. Vaginoplasty involves the excision of portions of mucosa from the vaginal fornices to tighten a relatively lax upper vagina.

These procedures require tissue ablation, which is achieved using tools including scalpel, needle electrode, or laser. Currently, laser energy is preferred over electrocautery or manual scalpel. This is due to several advantages observed by currently used 980 nm diode lasers and $CO_2$ 10.6 mm lasers, namely, wide surgical field for observation, minimum lesion in adjacent tissue allowing for fast cicatrization, minimum risk of complications, minimum percentage of recurrence and essentially immediate homeostasis. However, currently used laser devices present limitations. $CO_2$ lasers are large and bulky and have a complex and delicate arrangement of mirrors which are easily displaced. Furthermore their rigid structure does not allow physician to comfortably and accurately point at the desired target.

Penetration of 980 nm and 10.6 mm wavelengths to inner capillaries is undesirable when target tissue is on the surface. Another disadvantage of prior art is that currently used optical fibers emit in a forward direction. This limits physician in capability of accurate access to, for example, lateral walls inside vagina. Accuracy needs to be enhanced in order to decrease possibility of reported post-operative complications, such as infection, altered sensitivity, dyspareunia, adhesions, and scarring.

US Patent Application Publication 2007/0233191 by Parmer discloses a device and method of tightening tissue of the female genitalia by heating targeted connective tissue with radiant energy, while cooling the mucosal epithelial surface over the target tissue to protect it from the heat. As treatment tip contacts the epithelial mucosa, the tip cools the mucosa by contact, and delivers energy through the epithelium to the underlying tissue, creating a reverse thermal gradient. The desired effect is to remodel genital tissue by tightening it. Such remodeling may include a tighter vagina and a tighter introitus as a consequence of thermal denaturation of collagen as well as a longer term healing response in the tissue that includes an increased deposition of collagen. The types of energy delivery element may include a radiofrequency, microwave or ultrasound delivery. Mentioned types of energy are not ideal for treatment of female genitalia. They present several disadvantages in comparison with laser energy, related to precision and their effects on target tissue. Laser energy offers more accuracy, better coagulation effects and minimizes the need for cooling the mucosal epithelial surface this invention proposes.

Thus, a safe accurate and effective treatment system is needed for carrying out surgical ablation procedures to improve anatomical and physiological aspects of a woman's genitalia.

There is thus a need for a treatment system that improves on the state of the art, providing complete, safe, minimally invasive treatment for treating a woman's genitalia to achieve and enhance a woman's sexual expectations considering her vagina's physiological and anatomical condition, sex life and aesthetics. The present invention addresses these needs.

OBJECTIVES AND BRIEF SUMMARY OF THE INVENTION

It is an objective of the present invention to restore corporal integrity and biological functions of feminine genitalia for a renewed/rejuvenated sexuality that is more satisfactory, safe and pleasurable.

It is another objective of the present invention to provide a device and method of treatment for female sexual dysfunction (FSD).

It is also an objective of the present invention to provide a device and method for aesthetic enhancement of female genitalia.

It is yet another object of this invention to satisfy and enhance sexual gratification in women and their partners who may or may not suffer FSD.

It is still another objective of the present invention to present accurate laser energy to the interior of a woman's vagina to improve its anatomical and physiological characteristics for enhancement of the woman's sex life and that of her sexual partner.

Briefly stated, a device and method for treating a vagina's anatomic, functional and aesthetic conditions are disclosed. Device comprises a laser energy source which conveys laser energy through an optical fiber handpiece. A cylindrical or penis shaped device or applicator for insertion into the vagina, specially designed for safe and accurate irradiation of determined parts of vaginal mucosa is presented. Applicator has an inner hollow path through which optical fiber can be inserted to irradiate inner vaginal tissue. Irradiated mucous tissue contracts and vaginal radius is reduced and it thus can embrace penis in a tighter manner when penetration during sexual intercourse takes place. Consequently, sensitivity is substantially improved and sexual intercourse results more pleasurable for both the woman and her partner. In a preferred embodiment, a diode laser source is used emitting at 1470 nm. In another embodiment, vagina's outer dimensions are accurately measured and surgery is performed to achieve dimensions according to certain aesthetic and functional criteria. Present method and device causes minimum pain and risk of side effects. Procedure is ambulatory and can be carried out in a physician's office.

The above and other objects, features and advantages of the present invention will become apparent from the following description read in conjunction with the accompanying drawings.

DETAILED DESCRIPTION OF PREFERRED EMBODIMENTS

The present invention comprises a series of medical devices and treatments performed on the inside and the outside of a woman's vagina, based on the patient's expectations concerning quality of life, considering her physical health, psychological state, level of independence and social relations. Treatment is aimed mainly at women who have lost the normal shape of her genitals due to complicated labor, muscular dehiscence, or muscular tear, leading to loss of normal physiological conditions and a considerably decreased sexual response. Treatment is also aimed at women who wish to increase their self-esteem by aesthetically improving the looks of their vagina. Devices, method and criteria to achieve this are proposed without the drawbacks and limitations present in prior art.

After giving birth one or more times, women's vaginas become dilated or relaxed. The muscles are relaxed and have poor tone, strength, and control. During intercourse, dilated vaginas cannot embrace the penetrating penis properly and therefore sexual pleasure is diminished for both partners. Another important medical condition suffered by women with relaxed vaginas is vaginal prolapse, which can lead to other complications such as urinary incontinence. Applying laser energy within the vagina causes retraction of the mucosa, reducing its diameter by 15-20%. If the right energy is applied in certain places, it enhances pleasure during sexual intercourse or improves conditions like vaginal prolapse.

Figure 1:
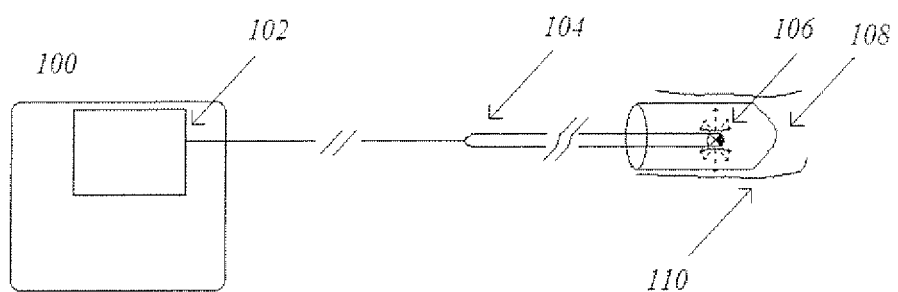
FIG. 1 Depicts a diagram of a preferred embodiment of present invention showing main comprising parts of laser system.

In a preferred embodiment, controlled vaginal hyperthermia (CVH) with a fiber optic medical treatment system is applied to enhance sexual gratification on women who for whatever reason lack an overall optimum architectural integrity of the vagina. FIG. 1 depicts a laser based system 100 comprising laser source 102 which emits at a preselected suitable wavelength through fiber optics device 104 radiating from its distal end 106 essentially perpendicular to the optical fiber axis. The type of optical fiber emission is chosen according to desired type of effect on tissue precision needed, maneuverability and convenient type of emitting pattern. Fibers used include a 360-degree radial fiber, a side firing fiber, an off-axis fiber or a twister fiber. In a preferred embodiment, a cylindrical penis-shaped accessory (applicator device) 108 is inserted inside vagina and is used such that fiber 104 emits radiation from within applicator/dilator 108 to assure accurate, safe and even radiation on vagina wall 110. Technique is preferably carried out with a low energy laser device operating at a preselected laser wavelength of about 1470±60 nm. The water content in target tissue assures high absorption of this wavelength and thus desired contraction effects with low energy values. In other embodiments different wavelengths are chosen, such as about 980±30 nm when, for example deeper tissue penetration is desired. Combinations of these two wavelengths as an example are beneficial when ablation and effectively deeper treatment of the tissue is needed in rejuvenation or corrective surgery.

Figure 2:
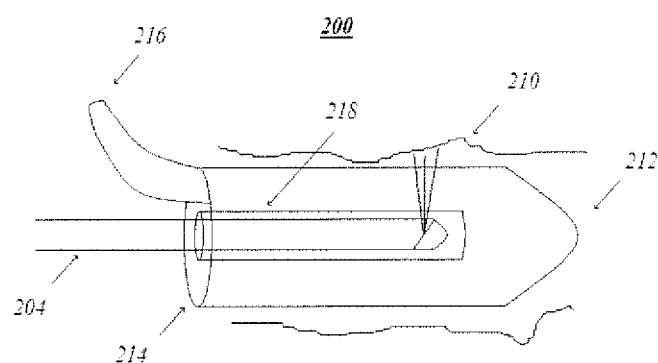
FIG. 2 Shows a diagram of one embodiment of special applicator device for irradiation within the vagina.

FIG. 2 shows applicator device previously mentioned, an essential instrument of a preferred embodiment of present invention used to assure that the procedure can be carried out accurately and safely. Applicator 200 comprises a specially designed cylindrical element, round-shaped or penis-shaped at insertion end 212 for easy placement into a vagina and a flat end at maneuvering end 214 preferably with a flap handle 216 for easy handling. Applicator 200 is longitudinally hollowed in the middle forming an inner hollow tube 218 such that an optical fiber 204 may be inserted up to about 7 cm into it. The vagina's internal mucous lining 210 (tunica mucosa) is irradiated from the inside using a side-firing fiber 204 at a 1470 nm wavelength at desired portions while avoiding irradiation of sensitive parts. In other preferred embodiments, inner tube 218 has a non-circular section, for example elliptical, rectangular or star-shaped. In this case, optical fiber is installed inside a hand piece holder with a similar section shape and size. This serves two purposes. First of all, it helps maintain fiber steady when applying radiation. Secondly, it prevents use of other commercially existing fibers not intended for application to this type of treatment, thus assuring patient safety.

Figure 3:
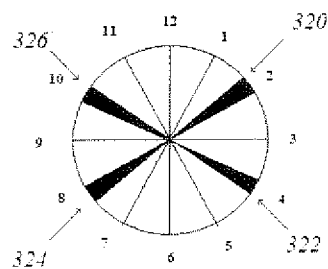
FIG. 3 Represents the "clock needle" positions of the tissue to be treated.

FIG. 3 represents the "clock needle" positions of the circumference 30 from which selected areas are to be irradiated. Target portions are located at 2 o'clock 320, 4 o'clock 322, 8 o'clock 324 and 10 o'clock 326. Portion between 10 o'clock 326 and 2 o'clock 320 must be avoided to protect the bladder. Portion between 4 o'clock 322 and 8 o'clock 324 must be avoided to protect the intestines. Thus, applying laser energy in the correct places causes controlled retraction of the mucosa in desired portions with minimal damage to underlying sensitive tissue and reduces a vagina's diameter.

FIG. 4a depicts another embodiment of essential applicator instrument of present invention used to assure procedure can be carried out accurately and safely. FIG. 4b represents a cross section of applicator 400. It comprises a specially designed cylindrical element 400, round-shaped or penis-shaped at insertion end 412 for easy placement into vagina and flat at maneuvering end 414 preferably with a flap 416 for easy handling. Applicator 400 is longitudinally hollowed in the middle forming inner hollow tube 418 such that optical fiber 404 may be inserted up to about 7 cm into it. A 360-degree radial emitting fiber or a side-firing fiber 404 is preferably used. As shown previously in FIG. 3, there are up to 4 longitudinal portions that should be irradiated, while other parts need to be preserved. Applicator 400 is designed such that its surface is transparent to light in places corresponding to target tissue areas 420 but opaque in the rest of the surface so that sensible organs are not reached by laser irradiation. Thus, a radial emitting fiber 404 is inserted through applicator 400 made of a material such that light goes through only transparent longitudinal canals 422 but is either reflected or absorbed in the rest of cylinder's internal wall.

Figure 4:
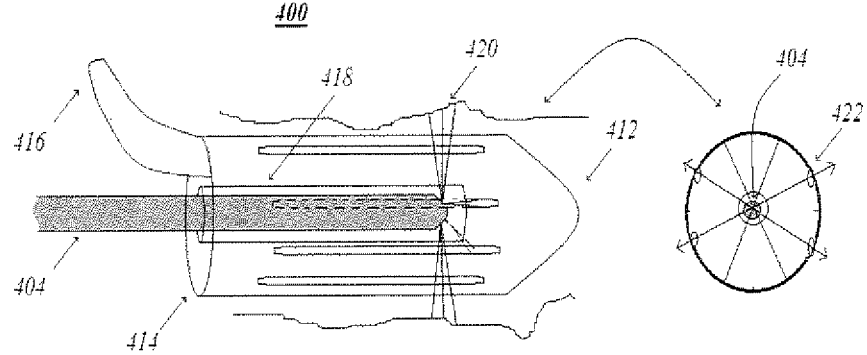
FIG. 4 Shows a diagram of another embodiment of special applicator device for irradiation within the vagina.

In a preferred embodiment, controlled vaginal hyperthermia (CVH) procedure consists of placing patient in gynecological position and introducing inside vagina an applicator device such as previously described FIG. 2 or FIG. 4. Next, fiber is introduced up to distal end of area to be treated. Additional elements such as a speculum can be used to aid in properly viewing treated area. Then, dilator is rotated to desired position and proper lasing parameters are set. Finally, laser energy is applied while fiber optic is withdrawn at a predetermined constant speed. After treatment, patient is encouraged to use a vaginal exerciser for a few days after surgery to prevent unwanted tissue collapse.

In another preferred embodiment, optical fiber is connected to an automatic pull-back system or device such as a step motor. This allows physician to assure withdrawal speed is constant, making procedure safer and more accurate.

In another preferred embodiment, applicator comprises an additional channel for insertion of an imaging system such as an endoscopic device, for online, real time monitoring of the procedure. An endoscopic device can also be incorporated through use of a shaped inner channel (hollow tube) to position both the endoscope and the fiber relative to one another in the main inner channel To further illustrate the present invention, the following example describes a device and procedure which has rendered positive tissue retraction results on women patients desiring enhancement of their sexual relations.

Example

A diode laser based system emitting at a wavelength of about 1470 nm was employed for controlled vaginal hyperthermia. Applicator is made of solid quartz, 3.5 cm in diameter and 10 cm long. It is flat on one end and rounded (penis-shaped) on the other end. It has a 7 cm long inner elliptical-shaped hollow tube in the middle with a transverse diameter of 2 mm and a conjugate diameter of 1 cm. Hand piece holder with a similar section shape and size and with a side-firing optical fiber fixed inside can fit inside hollow tube but does not allow fiber to rotate. Laser power is set at 10 Watts and emitted while fiber is withdrawn at a rate of 0.33 cm/s with firing end of fiber successively pointing at 4 o'clock, and at 10 o'clock. Endoscopic imaging after treatment showed a 5 mm thick white line along each lased portion of vaginal mucosa. Patient was instructed to not have sexual intercourse for the next 7 days. After a period of 45 days, lased portions retract and thus vaginal diameter is reduced.

Another area which can benefit from the device and procedure of the present invention is Vaginoplasty with laser radiation, which comprises enhancement of vulvar structures, namely labia minora, labia majora, mons veneris, vaginal aperture and hymen. Examples of treatments that comprise surgery are:

Reductive labiaplasty and reduction of excess clitoral hood procedures allow for reducing hypertrophy of labia minora, and correcting asymmetric labia.

Perineoplasty rejuvenates the perineum which has lost its tone, and improves the sagging labia majora and labia minora. This procedure aims to make the vulva look younger.

The device used is similar than the used in earlier examples/descriptions. Practitioners select optimally tipped fibers for use with given applicators and desired irradiation geometry. The power levels are similar for primarily denaturing tissue, though ablation would use somewhat higher power and/or longer exposure to deposit more energy and achieve the desired amount of ablative tissue.

Furthermore, vaginal relaxation causes other important medical conditions, such as prolapsed vaginal or pelvic areas, which are also beneficially treated by the present invention. A vaginal prolapse is a condition in which structures such as the uterus, rectum, bladder, urethra, small bowel, or the vagina itself may begin to prolapse, or fall out of their normal positions. Without medical treatment or surgery, these structures may eventually prolapse farther and farther into the vagina or even through the vaginal opening if their supports weaken enough. In their extreme they can become life-threatening. The symptoms that result from vaginal prolapse commonly affect sexual functions and bodily functions such as urination and defecation. Pelvic pressure and discomfort are also common symptoms. Urinary incontinence is a common symptom of this condition. In a preferred embodiment, minimally invasive surgery using 1470 nm laser radiation is applied to correct such medical conditions.

The overall objective is to treat the vagina so that it recovers its normal anatomy and physiology to achieve normal biological functions, improved external aspects and enhanced sexual gratification. Treatment is ambulatory and lasts a few minutes. Laser technique with 1470 nm or 980 nm wavelength and an off-axis or radially emitting fiber and protective device assures a precise treatment with minimal bleeding, effective scaring and essentially no complications or side effects. Final result is reconstruction of the most important part of the vagina for sexual pleasure, which is its lower third. Muscles and fascia are strengthened, thus improving vaginal muscular tone, strength and control. Excess vaginal mucosa is removed and the internal and external diameters of the vagina are reduced.

Two of the enhanced areas are directly or indirectly involved with areas that help produce an orgasm. One is the perineum, which is completely reconstructed, augmenting its potential for producing an orgasm. The other is the superior portion of the orgasmic platform, which contains the G-spot from which intense sexual pressure sensations derive.

In a preferred embodiment, surgery is aimed at recovering the harmony, proportion and symmetry of female genitalia by means of a determined consensus regarding aesthetic criteria such as the Binet Formula and the divine proportions of Vitruvius. Thus, the concept of $\varphi$, also named the aurial number, golden number or divine section, is considered to obtain optimal proportions of the vulva. This concept has been used by historically known geniuses such as Salvador Dali in his paintings and Leonardo Da Vinci in his works. In mathematics and the arts, two quantities are in the golden ratio if the ratio of the sum of the quantities to the larger quantity is equal to the ratio of the larger quantity to the smaller one. The golden ratio is an irrational mathematical constant, approximately 1.6180339887.

Figure 5:
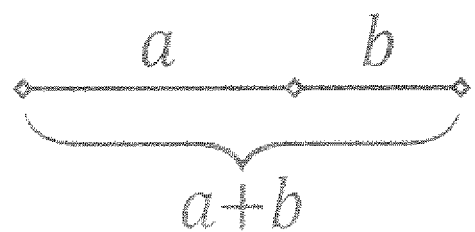
FIG. 5 Illustrates the geometric relationship that defines the Golden Ratio.

FIG. 5 illustrates the geometric relationship that defines this constant. Expressed algebraically:

$$\frac{a+b}{a} = \frac{a}{b} = \varphi.$$

This equation has as its unique positive solution, the algebraic irrational number $$\varphi = \frac{1+\sqrt{5}}{2} \approx 1.6180339887$$

The golden section is a line segment divided according to the golden ratio: The total length a+b is to the longer segment, a, as a is to the shorter segment, b.

Figure 6:
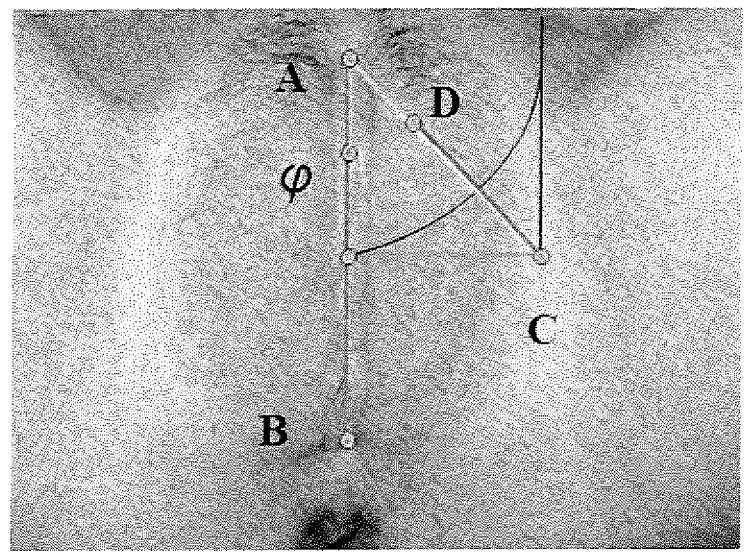
FIG. 6 Illustrates an example of the ideal location of the clitoris hood as a function of other parts of the female vagina.

FIG. 6 depicts an example of how, sequentially from A to D the ideal location of the clitoris hood is graphically located as a function of other parts of the female vagina.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A fiber optic medical treatment system for irradiating female genitalia comprising:
    at least one laser source capable of producing radiation at a preselected wavelength, a power level and a power density to irradiate human tissue;
    at least one optical fiber having an axis and optically coupled to said laser source and capable of transmitting said radiation from said laser source from proximal end to distal end of said optical fiber, said optical fiber being configured to emit said radiation from the distal end in a direction perpendicular to the fiber axis; and
    a cylindrical applicator device configured for inserting inside a vagina, having a surface and a longitudinal inner hollow tube into which said optical fiber can be moveably inserted and comprising in said surface at least one longitudinal canal transparent to laser radiation at the preselected wavelength, the rest of said surface reflecting or absorbing laser radiation at the preselected wavelength, whereby the vagina may be selectively irradiated with laser light through said at least one longitudinal canal transparent to laser light at the preselected wavelength as the optical fiber is withdrawn from the applicator device.

2. The fiber optic medical treatment system according to claim 1, further comprising:
    a handpiece to improve handling of said at least one optical fiber and aid in transmitting said radiation from distal end of said optical fiber.

3. The medical treatment system according to claim 1, wherein said preselected wavelength is selected from the group of about 1470±60 nm and about 980±30 nm or a combination of them.

4. The medical treatment system according to claim 1, wherein said optical fiber is selected from the group consisting of radial fibers, side firing fibers, twister fibers and off-axis fibers.

5. The medical treatment system according to claim 1, wherein said applicator device is rounded at insertion end.

6. The medical treatment system according to claim 1, whereby said inner hollow tube allows for insertion of a side firing optical fiber.

7. The medical treatment system according to claim 1, wherein said applicator device further comprises a canal for insertion of endoscopic imaging systems.

8. The medical treatment system according to claim 1, further comprising an automatic pullback device capable of withdrawing said optical fiber from said applicator device at a constant speed.

9. The medical treatment system according to claim 1, wherein said applicator device is configured to allow or prevent laser radiation at preselected "clock needle" positions useful in labiaplasty; perineoplasty; clitoral hood reduction; and vaginoplasty procedures.

10. The medical treatment system according to claim 9, wherein said system in vaginoplasty procedures includes a protective device when inside vagina, said system having a fiberoptic inside said protective device prior to applying laser radiation.

11. The medical treatment system according to claim 9, wherein said positions are selected to modify said genitalia's external appearance by measuring relative proportions of parts of said genitalia; applying the Golden Ratio as objective criteria for said genitalia's ideal said proportions; and emit laser radiation to achieve said ideal proportions.

12. The medical system according to claim 9, wherein said positions are selected to apply laser radiation internally to female genitalia for use in vaginal prolapsed and urinary incontinence treatments.

13. The medical treatment system according to claim 1, which comprises up to four transparent longitudinal canals, in said inner hollow tube.

* * * * *